US009943300B2

(12) United States Patent
McGuckin, Jr. et al.

(10) Patent No.: US 9,943,300 B2
(45) Date of Patent: *Apr. 17, 2018

(54) VASCULAR HOLE CLOSURE DEVICE

(71) Applicant: Rex Medical, L.P., Conshohocken, PA (US)

(72) Inventors: James F. McGuckin, Jr., Radnor, PA (US); John D. Leedle, Philadelphia, PA (US); James S. Tarmin, Philadelphia, PA (US); Thanu Anidharan, Downingtown, PA (US)

(73) Assignee: Rex Medical, L.P., Conshohocken, PA (US)

( * ) Notice: Subject to any disclaimer, the term of this patent is extended or adjusted under 35 U.S.C. 154(b) by 457 days.

This patent is subject to a terminal disclaimer.

(21) Appl. No.: 14/569,670

(22) Filed: Dec. 13, 2014

(65) Prior Publication Data

US 2015/0100082 A1   Apr. 9, 2015

Related U.S. Application Data

(60) Division of application No. 13/085,592, filed on Apr. 13, 2011, now Pat. No. 8,920,462, and a
(Continued)

(51) Int. Cl.
*A61B 17/00* (2006.01)
*A61B 17/04* (2006.01)

(52) U.S. Cl.
CPC ............... *A61B 17/0057* (2013.01); *A61B 2017/00004* (2013.01); *A61B 2017/00659* (2013.01);
(Continued)

(58) Field of Classification Search
CPC ........ A61B 17/0057; A61B 2017/0461; A61B 2017/0462; A61B 2017/0459;
(Continued)

(56) References Cited

U.S. PATENT DOCUMENTS 2,024,871 A   12/1935   Parsons
2,398,220 A    4/1946   Gelpcke
(Continued)

FOREIGN PATENT DOCUMENTS

AU   2011244878   5/2012
DE     19604817   8/1997
(Continued)

*Primary Examiner* — Dianne Dornbusch
(74) *Attorney, Agent, or Firm* — Neil D. Gershon

(57) ABSTRACT

A device for closing an aperture in a vessel wall, the aperture having an external opening in an external region of the vessel wall and an internal opening in an internal region of the vessel wall. The device includes a covering member positionable inside the vessel against the internal opening of the aperture and having a dimension to prevent egress of fluid through the aperture. First and second retainers are positionable external of the vessel and have a tip of a smaller transverse dimension and facing in a direction toward the covering member for advancement toward the covering member. A flexible connecting member operatively connects the covering member and the first retainer and moves the first retainer toward the covering member.

18 Claims, 4 Drawing Sheets

Related U.S. Application Data continuation-in-part of application No. 12/854,988, filed on Aug. 12, 2010, now abandoned, and a continuation-in-part of application No. 12/358,411, filed on Jan. 23, 2009, now Pat. No. 8,070,772.

(60) Provisional application No. 61/330,472, filed on May 3, 2010, provisional application No. 61/241,555, filed on Sep. 11, 2009, provisional application No. 61/066,072, filed on Feb. 15, 2008.

(52) U.S. Cl.
CPC .......... *A61B 2017/0456* (2013.01); *A61B 2017/0459* (2013.01)

(58) Field of Classification Search
CPC .... A61B 2017/0458; A61B 2017/0456; A61B 2017/0454; A61B 2017/0448; A61B 2017/0446; A61B 2017/00659; A61B 2017/00654; A61B 2017/00637; A61B 2017/00615; A61B 2017/0061; A61B 2017/00606; A61B 2017/00575
See application file for complete search history.

(56) References Cited

U.S. PATENT DOCUMENTS

| | | | |
|---|---|---|---|
| 2,413,142 | A | 12/1946 | Jones et al. |
| 3,454,004 | A | 7/1969 | Leininger et al. |
| 3,467,089 | A | 9/1969 | Hasson |
| 3,516,403 | A | 6/1970 | Cournut |
| 3,527,223 | A | 9/1970 | Shein |
| 3,675,648 | A | 7/1972 | Pharriss et al. |
| 3,842,826 | A | 10/1974 | Nolan |
| 3,842,827 | A | 10/1974 | Jacobs |
| 3,874,388 | A | 4/1975 | King et al. |
| 3,913,573 | A | 10/1975 | Gutnick |
| 3,937,217 | A | 2/1976 | Kosonen |
| 3,958,576 | A | 5/1976 | Komiya |
| 3,976,079 | A | 8/1976 | Samuels et al. |
| 4,007,743 | A | 2/1977 | Blake |
| 4,031,569 | A | 6/1977 | Jacob |
| 4,117,838 | A | 10/1978 | Hasson |
| 4,286,497 | A | 9/1981 | Shamah |
| 4,317,445 | A | 3/1982 | Robinson |
| 4,485,816 | A | 12/1984 | Krumme |
| 4,505,274 | A | 3/1985 | Speelman |
| 4,512,338 | A | 4/1985 | Balko et al. |
| 4,532,926 | A | 8/1985 | O'Holla |
| 4,610,671 | A | 9/1986 | Luther |
| 4,615,514 | A | 10/1986 | Hamlin |
| 4,638,803 | A | 1/1987 | Rand |
| 4,665,906 | A | 5/1987 | Jervis |
| 4,676,245 | A | 6/1987 | Fukuda |
| 4,705,040 | A * | 11/1987 | Mueller .......... A61B 17/00234 604/513 |
| 4,744,364 | A | 5/1988 | Kensey |
| 4,796,612 | A | 1/1989 | Reese |
| 4,836,204 | A | 6/1989 | Landymore et al. |
| 4,890,612 | A | 1/1990 | Kensey |
| 4,917,089 | A | 4/1990 | Sideris |
| 4,924,866 | A | 5/1990 | Yoon |
| 4,971,068 | A | 11/1990 | Sahi |
| 5,009,663 | A | 4/1991 | Broome |
| 5,021,059 | A | 6/1991 | Kensey et al. |
| 5,047,047 | A | 9/1991 | Yoon |
| 5,061,274 | A | 10/1991 | Kensey |
| 5,108,420 | A | 4/1992 | Marks |
| 5,108,421 | A | 4/1992 | Fowler |
| 5,123,913 | A | 6/1992 | Wilk et al. |
| 5,123,914 | A | 6/1992 | Cope |
| 5,171,252 | A | 12/1992 | Friedland |
| 5,171,259 | A | 12/1992 | Inoue |
| 5,192,300 | A | 3/1993 | Fowler |
| 5,192,301 | A | 3/1993 | Kamiya et al. |
| 5,192,302 | A | 3/1993 | Kensey et al. |
| 5,219,359 | A | 6/1993 | McQuilkin et al. |
| 5,222,974 | A | 6/1993 | Kensey et al. |
| 5,246,441 | A | 9/1993 | Ross et al. |
| 5,269,809 | A | 12/1993 | Hayhurst et al. |
| 5,279,572 | A | 1/1994 | Hokama |
| 5,282,827 | A | 2/1994 | Kensey et al. |
| 5,292,332 | A | 3/1994 | Lee |
| 5,306,254 | A | 4/1994 | Nash et al. |
| 5,312,435 | A | 5/1994 | Nash et al. |
| 5,318,040 | A | 6/1994 | Kensey et al. |
| 5,334,210 | A | 8/1994 | Gianturco |
| 5,350,399 | A | 9/1994 | Erlebacher et al. |
| 5,350,400 | A | 9/1994 | Esposito et al. |
| 5,370,661 | A | 12/1994 | Branch |
| 5,372,146 | A | 12/1994 | Branch |
| 5,385,554 | A | 1/1995 | Brimhall |
| RE34,866 | E | 2/1995 | Kensey et al. |
| 5,391,183 | A | 2/1995 | Janzen et al. |
| 5,409,444 | A | 4/1995 | Kensey et al. |
| 5,411,520 | A | 5/1995 | Nash et al. |
| 5,433,727 | A | 7/1995 | Sideris |
| 5,441,517 | A | 8/1995 | Kensey et al. |
| 5,443,481 | A | 8/1995 | Lee |
| 5,451,235 | A | 9/1995 | Lock et al. |
| 5,474,557 | A | 12/1995 | Mai |
| 5,478,352 | A | 12/1995 | Fowler |
| 5,478,353 | A | 12/1995 | Yoon |
| 5,486,195 | A | 1/1996 | Myers et al. |
| 5,507,754 | A | 4/1996 | Green et al. |
| 5,520,691 | A | 5/1996 | Branch |
| 5,531,759 | A | 7/1996 | Kensey et al. |
| 5,540,716 | A | 7/1996 | Hlavacek |
| 5,545,178 | A | 8/1996 | Kensey et al. |
| 5,549,617 | A | 8/1996 | Green et al. |
| 5,549,633 | A | 8/1996 | Evans et al. |
| 5,591,204 | A | 1/1997 | Janzen et al. |
| 5,593,422 | A | 1/1997 | Muijs Van de Moer et al. |
| 5,620,461 | A | 4/1997 | Muijs Van de Moer et al. |
| 5,630,833 | A | 5/1997 | Katsaros et al. |
| 5,634,936 | A | 6/1997 | Linden et al. |
| 5,643,317 | A | 7/1997 | Pavcnik et al. |
| 5,649,959 | A | 7/1997 | Hannam et al. |
| 5,658,313 | A | 8/1997 | Thal |
| 5,662,681 | A | 9/1997 | Nash et al. |
| 5,674,231 | A | 10/1997 | Green et al. |
| 5,676,689 | A | 10/1997 | Kensey et al. |
| 5,690,674 | A | 11/1997 | Diaz |
| 5,700,277 | A * | 12/1997 | Nash .................. A61B 17/0057 128/887 |
| 5,702,421 | A | 12/1997 | Schneidt |
| 5,707,393 | A | 1/1998 | Kensey et al. |
| 5,709,707 | A | 1/1998 | Lock et al. |
| 5,725,498 | A | 3/1998 | Janzen et al. |
| 5,728,132 | A | 3/1998 | Van Tassel et al. |
| 5,728,133 | A | 3/1998 | Kontos |
| 5,735,875 | A | 4/1998 | Bonutti et al. |
| 5,735,877 | A | 4/1998 | Pagedas |
| 5,741,223 | A | 4/1998 | Janzen |
| 5,741,297 | A | 4/1998 | Simon |
| 5,766,206 | A | 6/1998 | Wijkamp et al. |
| 5,769,894 | A | 6/1998 | Ferragamo |
| 5,782,600 | A | 7/1998 | Walsh |
| 5,782,860 | A | 7/1998 | Epstein et al. |
| 5,782,861 | A | 7/1998 | Cragg et al. |
| 5,810,845 | A | 9/1998 | Yoon |
| 5,810,846 | A | 9/1998 | Virnich et al. |
| 5,810,884 | A | 9/1998 | Kim |
| 5,814,056 | A | 9/1998 | Prosst et al. |
| 5,820,628 | A | 10/1998 | Middleman et al. |
| 5,861,003 | A | 1/1999 | Latson et al. |
| 5,893,856 | A | 4/1999 | Jacob et al. |
| 5,910,155 | A | 6/1999 | Ratcliff et al. |
| 5,916,235 | A | 6/1999 | Guglielmi |
| 5,916,236 | A | 6/1999 | Muijs Van de Moer et al. |
| 5,919,207 | A | 7/1999 | Taheri |
| 5,928,266 | A | 7/1999 | Kontos |
| 5,964,782 | A | 10/1999 | Lafontaine et al. |

(56) References Cited

U.S. PATENT DOCUMENTS

| | | |
|---|---|---|
| 5,976,159 A | 11/1999 | Bolduc et al. |
| 5,976,174 A | 11/1999 | Ruiz |
| 5,984,933 A | 11/1999 | Yoon |
| 5,984,949 A | 11/1999 | Levin |
| 5,989,268 A | 11/1999 | Pugsley, Jr. et al. |
| 6,001,110 A | 12/1999 | Adams |
| 6,007,563 A | 12/1999 | Nash et al. |
| 6,010,517 A | 1/2000 | Linden et al. |
| 6,015,417 A | 1/2000 | Reynolds, Jr. |
| 6,024,756 A | 2/2000 | Huebsch et al. |
| 6,033,427 A | 3/2000 | Lee |
| 6,045,551 A | 4/2000 | Bonutti |
| 6,048,357 A | 4/2000 | Kontos |
| 6,048,358 A | 4/2000 | Barak |
| 6,056,768 A | 5/2000 | Cates et al. |
| 6,063,085 A | 5/2000 | Tay et al. |
| 6,063,106 A | 5/2000 | Gibson |
| 6,066,160 A | 5/2000 | Colvin |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,110,207 A | 8/2000 | Eichhorn et al. |
| 6,113,611 A | 9/2000 | Allen et al. |
| 6,117,159 A | 9/2000 | Heubsch et al. |
| 6,117,161 A | 9/2000 | Li et al. |
| 6,120,524 A | 9/2000 | Taheri |
| 6,126,675 A | 10/2000 | Schervinsky et al. |
| 6,136,010 A | 10/2000 | Modseitt et al. |
| 6,139,564 A | 10/2000 | Teoh |
| 6,152,948 A | 11/2000 | Addis |
| 6,162,240 A | 12/2000 | Cates et al. |
| 6,171,320 B1 | 1/2001 | Monassevitch |
| 6,171,329 B1 | 1/2001 | Shaw et al. |
| 6,174,322 B1 | 1/2001 | Schneidt |
| 6,179,863 B1 | 1/2001 | Kensey et al. |
| 6,197,042 B1 | 3/2001 | Ginn et al. |
| 6,206,893 B1 | 3/2001 | Klein et al. |
| 6,206,907 B1 | 3/2001 | Marino et al. |
| 6,228,096 B1 | 5/2001 | Marchand |
| 6,231,561 B1 | 5/2001 | Frazier et al. |
| 6,231,592 B1 | 5/2001 | Bonutti et al. |
| 6,251,122 B1 | 6/2001 | Tsukernik |
| 6,261,309 B1 | 7/2001 | Urbanski |
| 6,264,673 B1 | 7/2001 | Egnelöv |
| 6,270,515 B1 | 8/2001 | Linden et al. |
| 6,277,140 B2 | 8/2001 | Ginn et al. |
| 6,290,674 B1 | 9/2001 | Roue et al. |
| 6,293,961 B2 | 9/2001 | Schwartz et al. |
| 6,312,446 B1 | 11/2001 | Huebsch |
| 6,328,727 B1 | 12/2001 | Frazier et al. |
| 6,334,865 B1 | 1/2002 | Redmond et al. |
| 6,336,914 B1 | 1/2002 | Gillespie et al. |
| 6,342,064 B1 | 1/2002 | Koike et al. |
| 6,346,117 B1 | 1/2002 | Baccaro |
| 6,348,053 B1 | 2/2002 | Cachia |
| 6,350,270 B1 | 2/2002 | Roue |
| 6,350,274 B1 | 2/2002 | Li |
| 6,355,052 B1 | 3/2002 | Neuss et al. |
| 6,368,341 B1 | 4/2002 | Abrahamson |
| 6,368,343 B1 | 4/2002 | Bonutti et al. |
| 6,391,037 B1 | 5/2002 | Greenhalgh |
| 6,391,048 B1 | 5/2002 | Ginn et al. |
| 6,409,739 B1 | 6/2002 | Nobles et al. |
| 6,414,664 B1 | 7/2002 | Conover et al. |
| 6,419,669 B1 | 7/2002 | Frazier et al. |
| 6,425,911 B1 | 7/2002 | Akerfeldt et al. |
| 6,436,088 B2 | 8/2002 | Frazier et al. |
| 6,440,152 B1 | 8/2002 | Gainor et al. |
| 6,447,042 B1 | 9/2002 | Jin |
| 6,447,524 B1 | 9/2002 | Knodel et al. |
| 6,451,030 B2 | 9/2002 | Li et al. |
| 6,468,293 B2 | 10/2002 | Bonutti et al. |
| 6,482,179 B1 | 11/2002 | Chu et al. |
| 6,491,714 B1 | 12/2002 | Bennett |
| 6,500,184 B1 | 12/2002 | Chan et al. |
| 6,508,828 B1 | 1/2003 | Akerfeldt et al. |
| 6,537,299 B1 | 3/2003 | Hogendijk et al. |
| 6,547,806 B1 | 4/2003 | Ding |
| 6,569,185 B2 | 5/2003 | Ungs |
| 6,569,187 B1 | 5/2003 | Bonutti et al. |
| 6,503,266 B1 | 7/2003 | Sjögren |
| 6,585,748 B1 | 7/2003 | Jeffree |
| 6,585,750 B2 | 7/2003 | Bonutti et al. |
| 6,596,012 B2 | 7/2003 | Akerfeldt et al. |
| 6,626,937 B1 | 9/2003 | Cox |
| 6,635,073 B2 | 10/2003 | Bonutti |
| 6,642,169 B2 | 11/2003 | Weatherhead |
| 6,648,903 B1 | 11/2003 | Pierson, III |
| 6,663,653 B2 | 12/2003 | Akerfeldt |
| 6,663,655 B2 | 12/2003 | Ginn |
| 6,676,685 B2 | 1/2004 | Pedros et al. |
| 6,682,489 B2 | 1/2004 | Tenerz et al. |
| 6,699,163 B2 | 3/2004 | Cope |
| 6,699,263 B2 | 3/2004 | Cope |
| 6,712,836 B1 | 3/2004 | Berg et al. |
| 6,712,837 B2 | 3/2004 | Akerfeldt et al. |
| 6,749,621 B2 | 6/2004 | Pantages et al. |
| 6,749,622 B2 | 6/2004 | McGuckin, Jr. et al. |
| 6,766,186 B1 | 7/2004 | Hoyns et al. |
| 6,786,915 B2 | 9/2004 | Akerfeldt et al. |
| 6,790,220 B2 | 9/2004 | Morris |
| 6,846,316 B2 | 1/2005 | Abrams |
| 6,855,153 B2 | 2/2005 | Saadat |
| 6,860,895 B1 | 3/2005 | Akerfeldt et al. |
| 6,863,680 B2 | 3/2005 | Ashby |
| 6,909,130 B2 | 6/2005 | Yoda et al. |
| 6,929,655 B2 | 8/2005 | Egnelöv |
| 6,932,835 B2 | 8/2005 | Bonutti et al. |
| 6,939,363 B2 | 9/2005 | Akerfeldt |
| 6,949,107 B2 | 9/2005 | McGuckin, Jr. et al. |
| 6,960,224 B2 | 11/2005 | Marino et al. |
| 6,972,027 B2 | 12/2005 | Fallin et al. |
| 6,984,219 B2 | 1/2006 | Ashby |
| 6,997,940 B2 | 2/2006 | Bonutti |
| 7,008,440 B2 | 3/2006 | Sing et al. |
| 7,008,442 B2 | 3/2006 | Brightbill |
| 7,025,756 B2 | 4/2006 | Frazier et al. |
| 7,025,776 B1 | 4/2006 | Houser et al. |
| 7,033,380 B2 | 4/2006 | Schwartz et al. |
| 7,033,393 B2 | 4/2006 | Gainor et al. |
| 7,048,748 B1 | 5/2006 | Ustuner |
| 7,048,755 B2 | 5/2006 | Bonutti et al. |
| 7,083,635 B2 | 8/2006 | Ginn |
| 7,087,073 B2 | 8/2006 | Bonutti |
| 7,094,209 B2 | 8/2006 | Egnelöv |
| 7,115,110 B2 | 10/2006 | Frazier et al. |
| 7,135,032 B2 | 11/2006 | Akerfeldt |
| 7,147,652 B2 | 12/2006 | Bonutti et al. |
| 7,150,757 B2 | 12/2006 | Fallin et al. |
| 7,153,323 B2 | 12/2006 | Teoh et al. |
| 7,169,168 B2 | 1/2007 | Muijs Van de Moer et al. |
| 7,175,648 B2 | 2/2007 | Nakao |
| 7,235,091 B2 | 6/2007 | Thornes |
| 7,267,679 B2 | 9/2007 | McGuckin, Jr. et al. |
| 7,285,097 B2 | 10/2007 | Tenerz |
| 7,288,105 B2 | 10/2007 | Oman et al. |
| 7,316,706 B2 | 1/2008 | Bloom et al. |
| 7,329,270 B2 | 2/2008 | Akerfeldt |
| 7,341,595 B2 | 3/2008 | Hinchliffe et al. |
| 7,361,183 B2 | 4/2008 | Ginn |
| 7,468,068 B2 | 12/2008 | Kolster |
| 7,488,340 B2 | 2/2009 | Kauphusman et al. |
| 7,530,990 B2 | 5/2009 | Perriello et al. |
| 7,566,339 B2 | 7/2009 | Kolster |
| 7,582,105 B2 | 9/2009 | Kolster |
| 7,594,923 B2 | 9/2009 | Fallin et al. |
| 7,597,705 B2 | 10/2009 | Forrsberg et al. |
| 7,618,435 B2 | 11/2009 | Raschdorf, Jr. |
| 7,618,438 B2 | 11/2009 | White et al. |
| 7,621,937 B2 | 11/2009 | Pipenhagenet et al. |
| 7,625,352 B1 | 12/2009 | Ashby et al. |
| 7,637,921 B2 | 12/2009 | Akerfeldt |

(56) References Cited

U.S. PATENT DOCUMENTS

| | | |
|---|---|---|
| 7,654,963 B2 | 2/2010 | Egnelöv |
| 7,658,751 B2 | 2/2010 | Stone et al. |
| 7,662,160 B2 | 2/2010 | Bojarski et al. |
| 7,662,161 B2 | 2/2010 | Briganti et al. |
| 7,666,199 B2 | 2/2010 | McIntyer |
| 7,717,929 B2 | 5/2010 | Fallman |
| 7,736,378 B2 | 6/2010 | Maahs et al. |
| 7,758,594 B2 | 7/2010 | Lamson et al. |
| 7,775,988 B2 | 8/2010 | Pijls |
| 7,780,699 B2 | 8/2010 | Zhu |
| 7,824,417 B2 | 11/2010 | Magnusson |
| 7,846,180 B2 | 12/2010 | Cerier |
| 7,862,584 B2 | 1/2011 | Lyons |
| 7,931,670 B2 | 4/2011 | Fiehler |
| 7,931,671 B2 | 4/2011 | Tenerz |
| 7,938,846 B2 | 5/2011 | Akerfeldt |
| 7,967,840 B2 | 6/2011 | Chanduszko |
| 8,016,857 B2 | 9/2011 | Satar |
| 8,070,772 B2 | 12/2011 | McGuckin et al. |
| 8,088,143 B2 | 1/2012 | Akerfeldt |
| 8,105,352 B2 | 1/2012 | Egnelöv |
| 8,109,968 B2 | 2/2012 | Ashley |
| 8,118,831 B2 | 2/2012 | Egnelöv |
| 8,118,832 B1 | 2/2012 | Morris |
| 8,118,833 B2 | 2/2012 | Seibold |
| 8,267,959 B2 | 9/2012 | Fällman |
| 8,308,762 B2 | 11/2012 | Mahlin |
| 8,348,971 B2 | 1/2013 | Khanna et al. |
| 8,382,793 B2 | 2/2013 | Egnelöv |
| 8,398,675 B2 | 3/2013 | Egnelöv |
| 8,444,673 B2 | 5/2013 | Thielen et al. |
| RE44,297 E | 6/2013 | Akerfeldt |
| 8,469,944 B2 | 6/2013 | Mahlin |
| 8,480,686 B2 | 7/2013 | Bakos |
| 8,647,365 B2 | 2/2014 | Tegels |
| 8,652,166 B2 | 2/2014 | Akerfeldt |
| 8,663,254 B2 | 3/2014 | Feussner |
| 8,685,059 B2 | 4/2014 | Walters |
| 8,870,917 B2 | 10/2014 | Walters |
| 9,039,738 B2 | 5/2015 | Pipenhagen et al. |
| 2001/0010005 A1 | 7/2001 | Kammerer |
| 2002/0055767 A1 | 5/2002 | Forde |
| 2002/0082622 A1 | 6/2002 | Kane |
| 2002/0095179 A1 | 7/2002 | Tenerz et al. |
| 2002/0165561 A1 | 11/2002 | Ainsworth et al. |
| 2002/0165572 A1 | 11/2002 | Saadat |
| 2002/0183787 A1 | 12/2002 | Wahr et al. |
| 2003/0009180 A1 | 1/2003 | Hinchliffe et al. |
| 2003/0050665 A1 | 3/2003 | Ginn |
| 2003/0055451 A1 | 3/2003 | Jones et al. |
| 2003/0088256 A1 | 5/2003 | Conston et al. |
| 2003/0088269 A1 | 5/2003 | Ashby |
| 2003/0105487 A1 | 6/2003 | Benz et al. |
| 2003/0125031 A1 | 7/2003 | Sung Lim et al. |
| 2003/0130694 A1 | 7/2003 | Bojarski et al. |
| 2003/0144695 A1 | 7/2003 | McGuckin, Jr. et al. |
| 2003/0187473 A1 | 10/2003 | Berenstein et al. |
| 2003/0191495 A1 | 10/2003 | Ryan et al. |
| 2004/0002764 A1 | 1/2004 | Gainer et al. |
| 2004/0010287 A1 | 1/2004 | Bonutti |
| 2004/0039413 A1 | 2/2004 | Akerfeldt |
| 2004/0049207 A1 | 3/2004 | Goldfarb |
| 2004/0093025 A1 | 5/2004 | Egnalov |
| 2004/0133236 A1 | 7/2004 | Chanduszko |
| 2004/0133238 A1 | 7/2004 | Cerier |
| 2004/0143294 A1 | 7/2004 | Corcoran et al. |
| 2004/0158287 A1 | 8/2004 | Cragg et al. |
| 2004/0153103 A1 | 9/2004 | Schwartz et al. |
| 2004/0176800 A1 | 9/2004 | Paraschac et al. |
| 2004/0230223 A1 | 11/2004 | Bonutti et al. |
| 2005/0033326 A1 | 2/2005 | Briganti |
| 2005/0059982 A1 | 3/2005 | Zung et al. |
| 2005/0065547 A1 | 3/2005 | Marino et al. |
| 2005/0070957 A1 | 3/2005 | Das |
| 2005/0075654 A1 | 4/2005 | Kelleher |
| 2005/0085852 A1 | 4/2005 | Ditter |
| 2005/0085855 A1 | 4/2005 | Forsberg |
| 2005/0090859 A1 | 4/2005 | Ravlkumar |
| 2005/0096696 A1 | 5/2005 | Forsberg |
| 2005/0096697 A1 | 5/2005 | Forsberg |
| 2005/0107807 A1 | 5/2005 | Nakao |
| 2005/0125030 A1 | 6/2005 | Forsberg et al. |
| 2005/0125032 A1 | 6/2005 | Whisenant et al. |
| 2005/0169974 A1 | 8/2005 | Tenerz et al. |
| 2005/0177182 A1 | 8/2005 | van der Burg et al. |
| 2005/0192627 A1 | 9/2005 | Whisenant et al. |
| 2005/0192630 A1 | 9/2005 | Maas et al. |
| 2005/0216059 A1 | 9/2005 | Bonutti |
| 2005/0267524 A1 | 12/2005 | Chanduszko |
| 2005/0267533 A1 | 12/2005 | Gertner |
| 2005/0283193 A1 | 12/2005 | Tullberg et al. |
| 2005/0288786 A1 | 12/2005 | Chanduszko |
| 2006/0069408 A1 | 3/2006 | Kato |
| 2006/0100665 A1 | 5/2006 | Von Oepen et al. |
| 2006/0106418 A1 | 5/2006 | Seibold et al. |
| 2006/0135991 A1 | 6/2006 | Kawaura |
| 2006/0142797 A1 | 6/2006 | Egnelov |
| 2006/0155327 A1 | 7/2006 | Briganti |
| 2006/0167495 A1 | 7/2006 | Bonutti et al. |
| 2006/0173492 A1 | 8/2006 | Akerfeldt et al. |
| 2006/0212073 A1 | 9/2006 | Bonutti et al. |
| 2006/0217760 A1 | 9/2006 | Widomski et al. |
| 2006/0217765 A1 | 9/2006 | Bonutti et al. |
| 2006/0241695 A1 | 10/2006 | Bonutti et al. |
| 2006/0265009 A1 | 11/2006 | Bonutti |
| 2006/0271105 A1 | 11/2006 | Foerster et al. |
| 2006/0276871 A1 | 12/2006 | Lamson et al. |
| 2007/0010851 A1 | 1/2007 | Chanduszko |
| 2007/0010857 A1 | 1/2007 | Sugimoto et al. |
| 2007/0060858 A1 | 3/2007 | Sogard et al. |
| 2007/0073322 A1 | 3/2007 | Mikkaichi et al. |
| 2007/0073337 A1 | 3/2007 | Abbott |
| 2007/0088388 A1 | 4/2007 | Opolski |
| 2007/0135826 A1 | 6/2007 | Zaver |
| 2007/0149987 A1 | 6/2007 | Wellman et al. |
| 2007/0149998 A1 | 6/2007 | Wicks et al. |
| 2007/0149999 A1 | 6/2007 | Szabo et al. |
| 2007/0150002 A1 | 6/2007 | Szabo et al. |
| 2007/0156175 A1 | 7/2007 | Weadock |
| 2007/0185529 A1 | 8/2007 | Coleman |
| 2007/0185532 A1 | 8/2007 | Stone et al. |
| 2007/0198038 A1 | 8/2007 | Cohen |
| 2007/0239208 A1 | 10/2007 | Crawford |
| 2007/0239209 A1 | 10/2007 | Fallman |
| 2007/0244518 A1 | 10/2007 | Callaghan |
| 2007/0255316 A1 | 11/2007 | McIntyre |
| 2007/0276437 A1 | 11/2007 | Call |
| 2008/0071310 A1 | 3/2008 | Hoffman et al. |
| 2008/0082128 A1 | 4/2008 | Stone |
| 2008/0114395 A1 | 5/2008 | Mathisen |
| 2008/0140092 A1 | 6/2008 | Stone et al. |
| 2008/0243182 A1 | 10/2008 | Bates |
| 2009/0030450 A1 | 1/2009 | Preinitz et al. |
| 2009/0036919 A1 | 2/2009 | Preinitz et al. |
| 2009/0036920 A1 | 2/2009 | Preinitz et al. |
| 2009/0043333 A1 | 2/2009 | Preinitz et al. |
| 2009/0076541 A1 | 3/2009 | Chin |
| 2009/0088778 A1 | 4/2009 | Miyamoto |
| 2009/0163934 A1 | 6/2009 | Raschdorf, Jr. |
| 2009/0177225 A1 | 7/2009 | Nunnez et al. |
| 2009/0216266 A1 | 8/2009 | Maruyama et al. |
| 2009/0216267 A1 | 8/2009 | Willard |
| 2009/0210004 A1 | 9/2009 | McGuckin, Jr. et al. |
| 2009/0234377 A1 | 9/2009 | Mahlin et al. |
| 2009/0248064 A1 | 10/2009 | Preinitz |
| 2009/0326460 A1 | 12/2009 | Beardsley |
| 2010/0114156 A1 | 5/2010 | Mehl |
| 2010/0312224 A1 | 12/2010 | Atthoff et al. |
| 2011/0071551 A1 | 3/2011 | Singhatat |
| 2011/0270307 A1 | 3/2011 | Szabo |
| 2011/0082495 A1 | 4/2011 | Ruiz |
| 2012/0078294 A1 | 3/2012 | Tarmin et al. |

(56) References Cited

U.S. PATENT DOCUMENTS

2013/0178895 A1    7/2013   Walters et al.
2014/0025021 A1    1/2014   Walters et al.

FOREIGN PATENT DOCUMENTS

| | | |
|---|---|---|
| EP | 0637431 | 2/1995 |
| EP | 0920842 | 6/1999 |
| EP | 1671592 | 6/2006 |
| EP | 2055236 | 5/2009 |
| EP | 2294986 | 3/2011 |
| EP | 2412317 | 2/2012 |
| WO | 9520913 | 8/1995 |
| WO | WO 95/32670 | 12/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | WO 01/40348 | 11/2000 |
| WO | WO 2001/021247 | 3/2001 |
| WO | WO 2004/012601 | 2/2004 |
| WO | WO 2004/098418 | 11/2004 |
| WO | 0112864 | 12/2004 |
| WO | WO 2006/093970 | 9/2006 |
| WO | WO 2009/108750 | 9/2009 |

\* cited by examiner

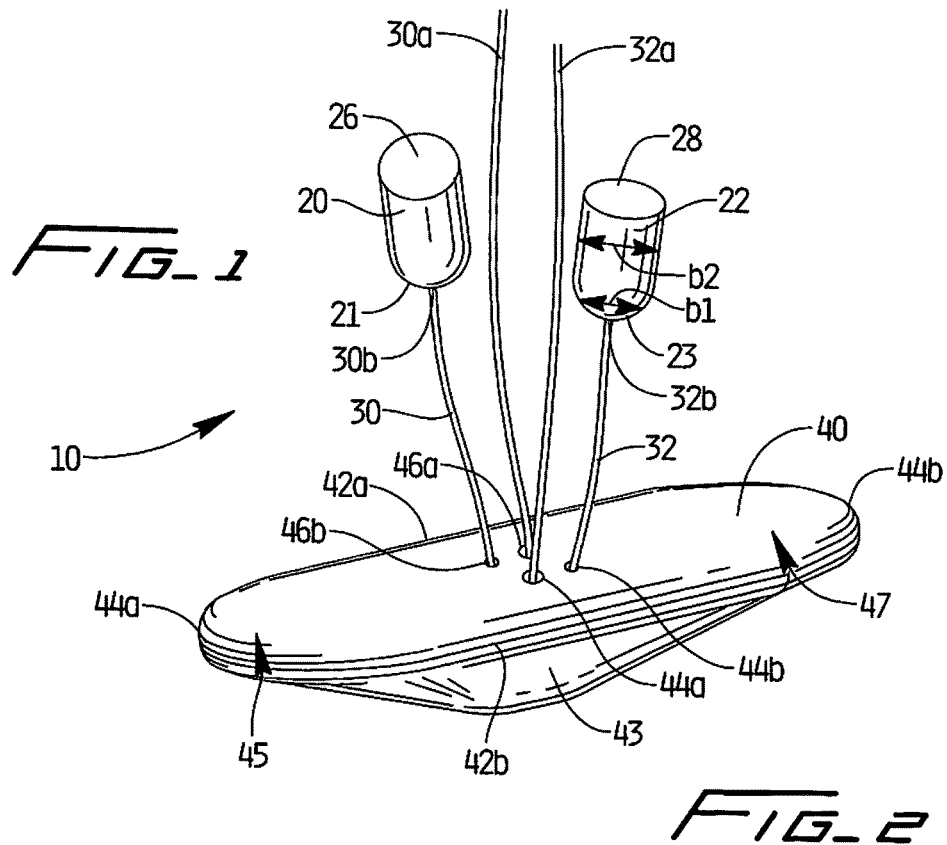
FIG_1
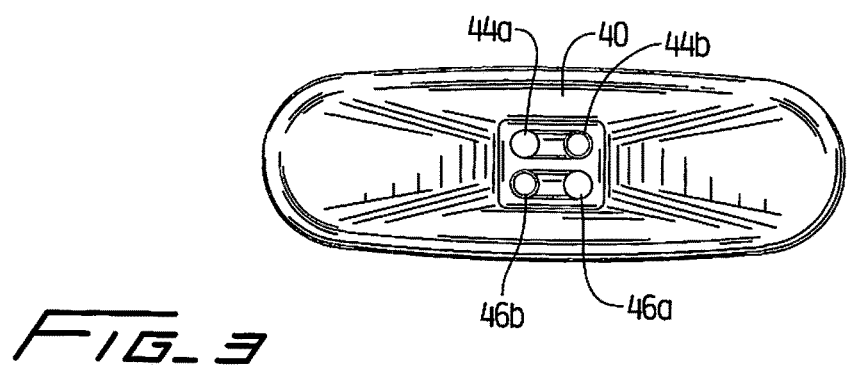
FIG_2
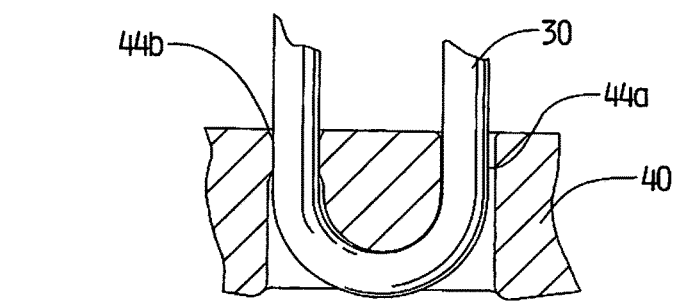
FIG_3

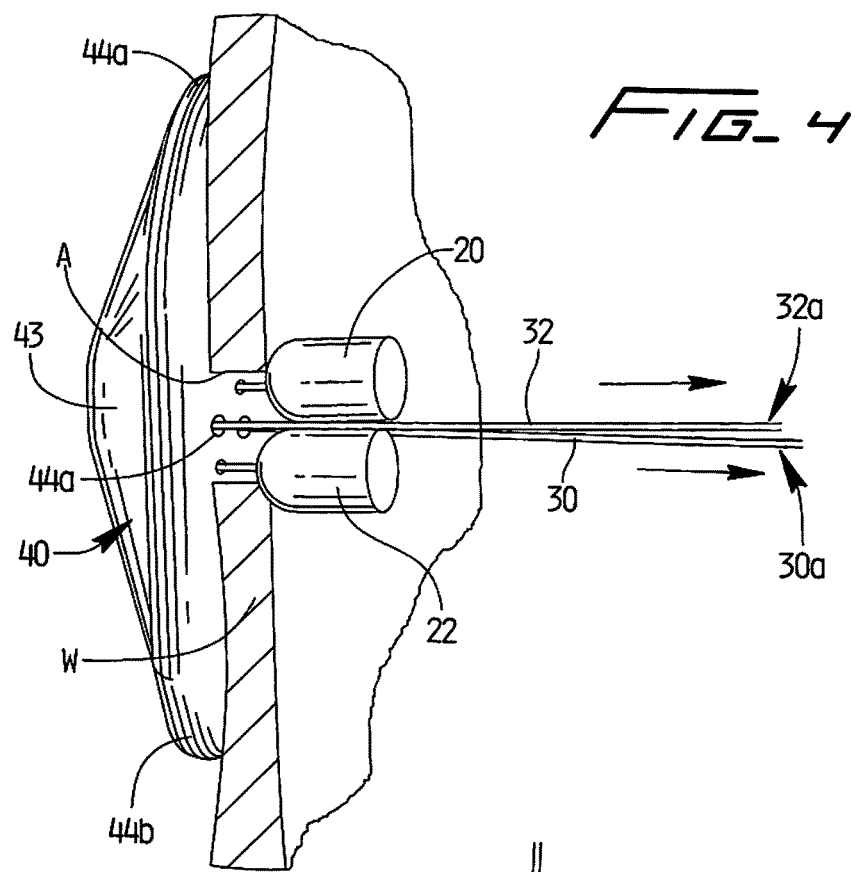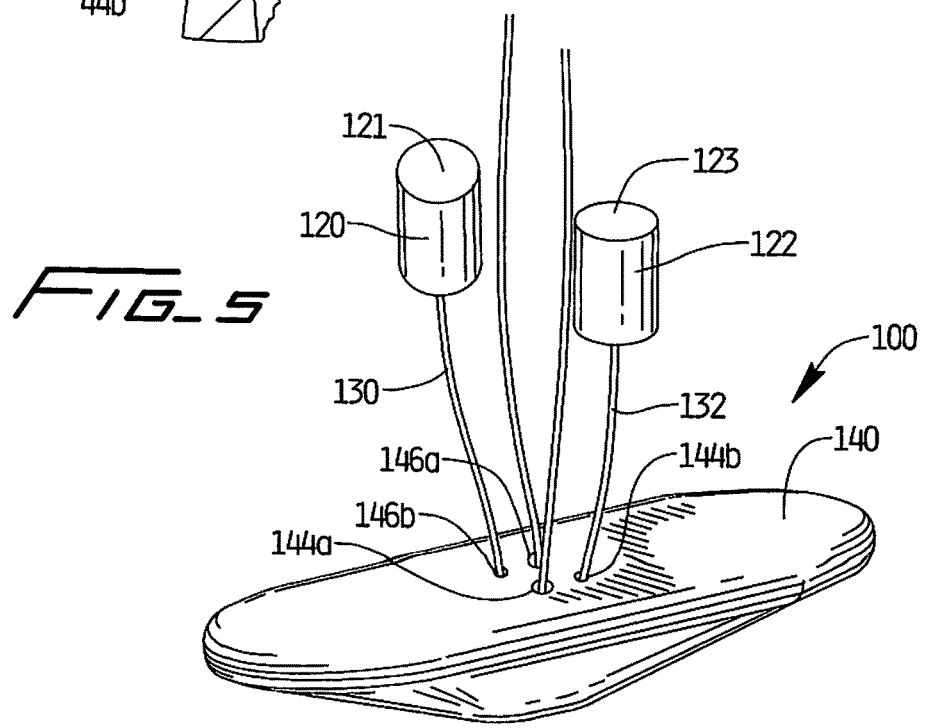

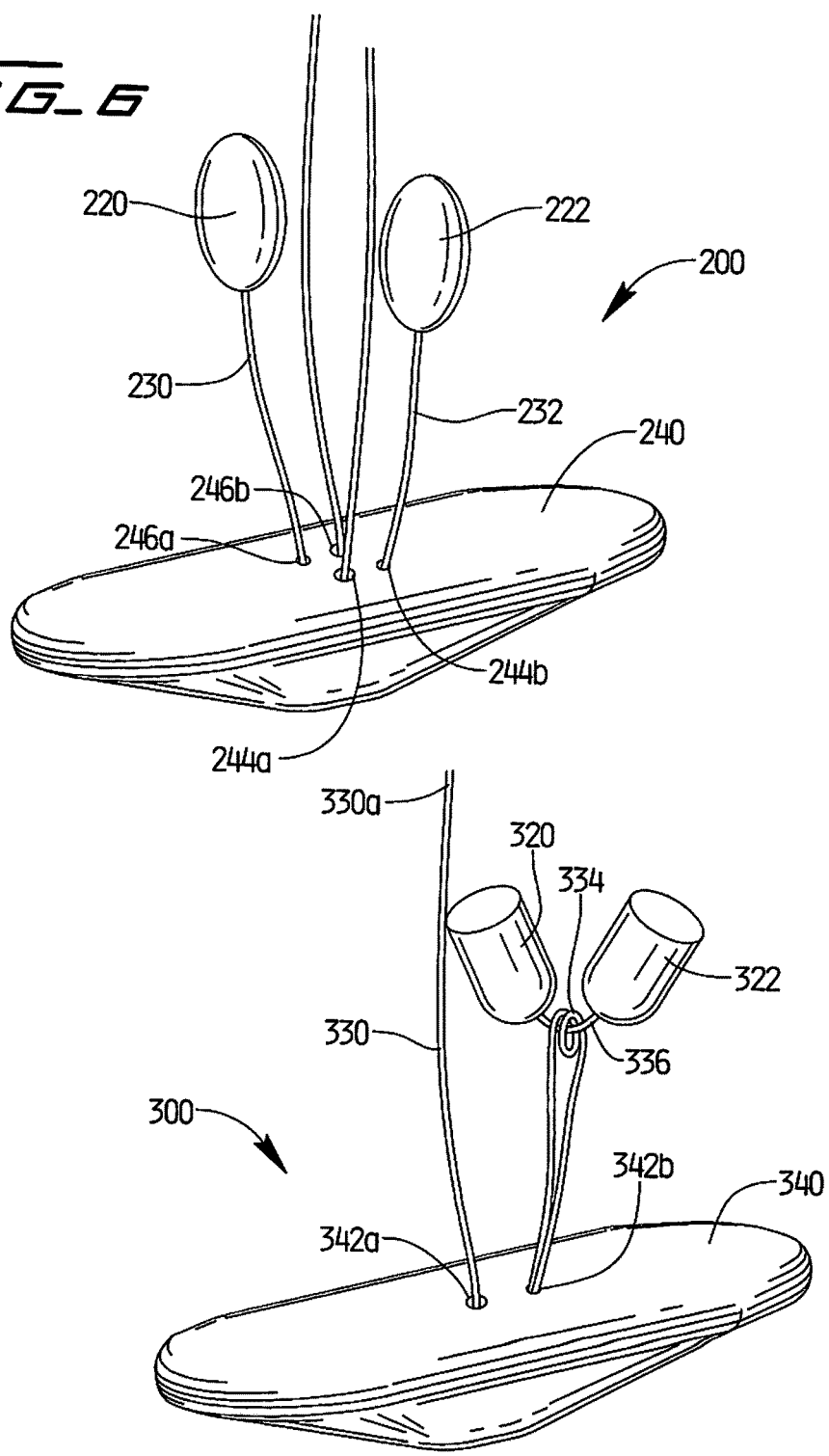

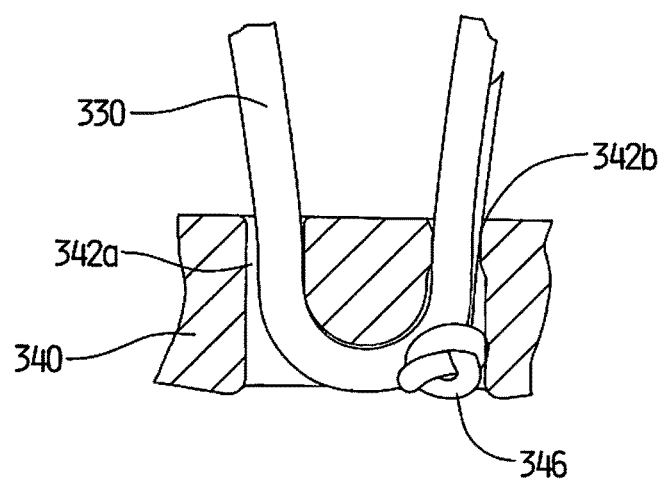
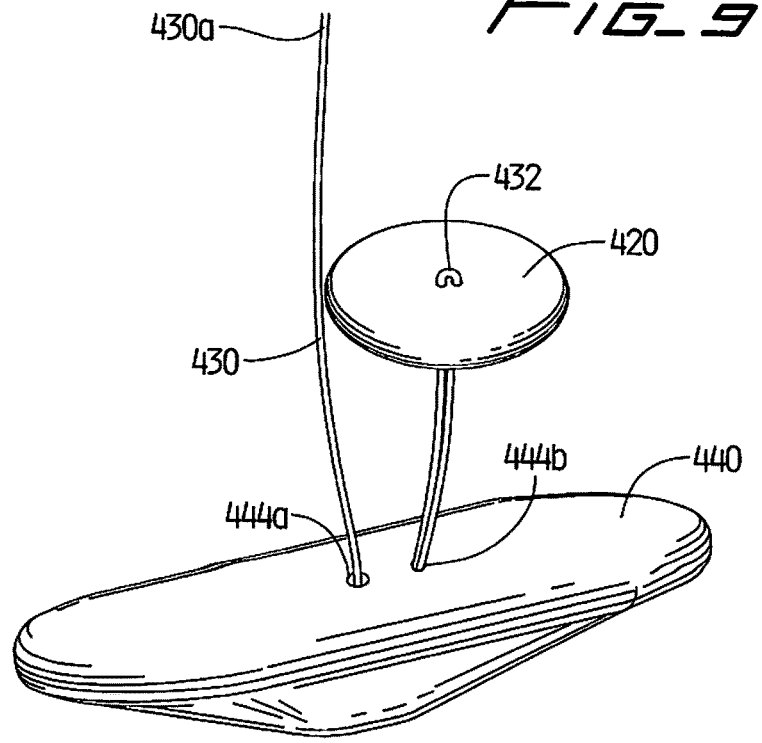

VASCULAR HOLE CLOSURE DEVICE

BACKGROUND

This application is divisional of application Ser. No. 13/085,592, filed Apr. 13, 2011, now U.S. Pat. No. 8,920,462, which claims priority from provisional application Ser. No. 61/330,472, filed May 3, 2010 and is a continuation in part of application Ser. No. 12/854,988, filed Aug. 12, 2010, now abandoned, which claims priority from provisional application Ser. No. 61/241,555, filed Sep. 11, 2009, and is a continuation in part of application Ser. No. 12/358,411, filed Jan. 23, 2009, now U.S. Pat. No. 8,070,772, which claims priority from provisional application Ser No. 61/066,072, filed Feb. 15, 2008. The entire contents of each of these applications are incorporated herein by reference.

TECHNICAL FIELD

This application relates to a vascular device and more particularly to a device for closing openings in vessel walls.

BACKGROUND OF RELATED ART

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, sold by Abbott, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally. the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned co-pending patent application Ser. No. 10/847,141, filed May 17, 2004, discloses effective vascular hole closure devices which have the foregoing advantages. It would be further advantageous to provide a vascular hole closure device which is adjustable to accommodate different tissue thicknesses and applies a more constant clamping/retaining force between the intravascular and extravascular components of the device irrespective of tissue thickness.

SUMMARY

The present invention provides a device for closing an aperture in a vessel wall, the aperture having an external opening in an external region of the vessel wall and an internal opening in an internal region of the vessel wall. The device comprises a covering member positionable inside the vessel against the internal opening of the aperture and having a dimension to prevent egress of fluid through the aperture, and first and second retainers positionable external of the vessel and each having a body of a first transverse dimension and a tip having a second smaller transverse dimension and facing in a direction toward the covering member for advancement toward the covering member. A flexible connecting member operatively connects the covering member and the first retainer and moves the first retainer toward the covering member.

In one embodiment, a first opening of the covering member is configured to restrict movement of the connecting member. The device may include a second flexible connecting member operatively connecting the covering member and second retainer for moving the second retainer toward the covering member.

In a preferred embodiment, the covering member is composed of a resorbable material. In a preferred embodiment, the flexible connecting members and retainers are composed of a resorbable material.

In one embodiment, the retainers are connected to each other by a flexible joining member, and the flexible connecting member includes a suture looped through the covering member and a looped portion to receive the flexible joining member, wherein tensioning of the suture tightens the looped portion and moves the joining member and retainers toward the covering member.

In another aspect, the present invention provides a device for closing an aperture in a vessel wall, the aperture having an external opening in an external region of the vessel wall and an internal opening in an internal region of the vessel wall. The device comprises a covering member positionable inside the vessel against the internal opening of the aperture and having a dimension to prevent egress of fluid through the aperture. First and second retainers being one of substantially cylindrical shaped and pill shaped are positionable external of the vessel and a flexible connecting member connects the first retainer to the covering member.

Preferably, pulling of the connecting member advances the first retainer toward the covering member. The covering member in some embodiments can have a second opening configured to restrict movement of the connecting member.

In some embodiments, a second connecting member connects the second retainer to the covering member.

Preferably, the covering member and the first and second retainers are composed of a resorbable material.

In one embodiment, the retainers are positioned in a stacked relationship in a delivery position.

The covering member is preferably pivotable between a more longitudinal orientation for delivery and a transverse position for placement.

In another aspect, the present invention provides a device for closing an aperture in a vessel wall, the aperture having an external opening in an external region of the vessel wall and an internal opening in an internal region of the vessel wall. The device comprises a covering member positionable inside the vessel against the internal opening of the aperture and has a dimension to prevent egress of fluid through the aperture and has a first opening of a first diameter and a second opening of a second larger diameter. A disc shaped retainer is provided for positioning external of the vessel lumen. A flexible connecting member operatively connects the retainer to the covering member and extends through the first and second openings and is connected to the retainer. The first opening is configured to frictionally retain the flexible member to retain the position of the retainer with respect to the covering member.

In another aspect, the present invention provides a device for closing an aperture in a vessel wall, the aperture having an external opening in an external region of the vessel wall and an internal opening in an internal region of the vessel wall. The device comprises a covering member positionable inside the vessel against the internal opening of the aperture and has a dimension to prevent egress of fluid through the aperture. First and second retainers are positionable external of the vessel and a joining member connects the first and second retainers. A flexible connecting member has a looped portion for receiving the joining member, wherein movement of the flexible connecting member moves the retainers toward the covering member.

In another aspect the present invention provides a method of closing an aperture in a vessel wall, the aperture having an external opening in an external region of the vessel wall and an internal opening in an internal region of the vessel wall, the method comprising:

inserting a covering member inside the vessel against the internal opening of the aperture, the covering member having a dimension to prevent egress of fluid through the aperture and having a connecting member extending therefrom;

inserting a first retainer external of the vessel; and applying a sufficient force to overcome resistance to movement of the connecting member to advance the first retainer toward the covering member.

In a preferred embodiment, the step of advancing the first retainer comprises the step of moving a suture attached to the first retainer through an opening having a diameter substantially the same as the outer diameter of the suture. The method may include the step of inserting a second retainer external of the vessel and advancing the second retainer toward the covering member by pulling a suture connected to the second retainer.

BRIEF DESCRIPTION OF THE DRAWINGS

Preferred embodiment(s) of the present disclosure are described herein with reference to the drawings wherein:

FIG. 1 is a perspective view of a first embodiment of the closure device of the present invention;

FIG. 2 is a bottom view of the covering member of the closure device of FIG. 1;

FIG. 3 is a cross-sectional view illustrating the suture extending through the covering member of FIG. 1;

FIG. 4 is a perspective view illustrating the sutures pulled proximally to move the retainers toward the covering member for positioning in a side by side relationship against the outer surface of the vessel wall;

FIG. 5 is a perspective view of a second embodiment of the closure device of the present invention;

FIG. 6 is a perspective view of another alternate embodiment of the closure device of the present invention;

FIG. 7 is a perspective view of a yet another alternate embodiment of the closure device of the present invention;

FIG. 8 is a cross-sectional view illustrating the suture of FIG. 7 extending through the covering member; and FIG. 9 is a perspective view of a yet another alternate embodiment of the closure device of the present invention.

DETAILED DESCRIPTION OF PREFERRED EMBODIMENTS

Referring now in detail to the drawings where like reference numerals identify similar or like components throughout the several views, FIG. 1 is a perspective view of a first embodiment of the vascular hole (aperture) closure device of the present invention. The device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure device of the present invention has an intravascular component to block blood flow and an extravascular component to retain the intravascular component.

More specifically, the closure device includes a covering member or patch positioned within the vessel against the internal wall of the vessel to block blood flow and two retainers positioned external of the vessel wall to retain the covering member in its blocking position. Each retainer is fixedly attached to a suture such that pulling of the suture advances the attached retainer toward the covering member to ultimately position the retainers in a side by side relationship either against or adjacent the external surface of the vessel wall.

Turning to FIGS. 1-4, a first embodiment of the closure device of the present invention is illustrated. Hole (aperture) closure device 10 has a covering member or patch 40, a first retainer 20 and a second retainer 22. The retainers 20, 22 are substantially bullet shaped with a substantially bullet nose portion 21, 23 respectively, to facilitate movement of the retainers 20, 22 toward the covering member 40. Thus, the tip of the retainers 20, 22 has a smaller transverse dimension than the body (Compare for example b1 and b2 of FIG. 1). The opposing end of the retainers 20, 22 can have a substantially planar surface 26, 28, respectively, although radiused surfaces or irregular surfaces are also contemplated. Covering member 40 is dimensioned and configured for positioning inside the vessel on the internal side of the vessel aperture against the internal wall of the vessel; the retainers 20, 22 are configured to be positioned outside the vessel wall adjacent or contiguous the external side of the vessel aperture.

Covering member 40, preferably elongated in configuration as shown, is retained in a delivery sheath in a longitudinal position for delivery to the vessel, and then pivots to a transverse position within the vessel lumen (substantially perpendicular to an axis extending through the aperture) for orientation to cover (patch) the vessel aperture on the internal side. This movement is illustrated in FIGS. 37A-37D of commonly assigned co-pending patent application Ser. No. 10/847,141, filed May 17, 2004, and issued as U.S. Pat. No. 7,662,161, the entire contents of which are incorporated herein by reference (hereinafter the '141 application).

The retainers 20, 22 are preferably held in a delivery tube in a stacked relationship (not shown), with retainer 22 atop retainer 20 (or vice versa).

The elongated covering member 40 functions to cover (patch) the internal opening in the vessel wall to prevent the egress of blood. With reference to FIG. 1, the covering member 40 is preferably somewhat oval shaped with elongated substantially parallel side walls 42a, 42b and end walls 49a, 49b connecting the side walls 42a, 42b. Other shapes of the covering member are also contemplated. Covering member preferably has a thicker region 43 in the central region than the first and second end regions 45, 47. Other dimensions are also contemplated.

The longitudinal axis of covering member 40 defines a lengthwise dimension and transverse axes define a shorter widthwise dimensions. The widthwise dimension of the covering member 40 can be for example about 2.5 mm (for a 6 Fr device). In a preferred embodiment, the covering member 40 is about 3.1 mm in widthwise dimension. Other dimensions are also contemplated. The width preferably is at least substantially equal to the dimension of the internal opening in the vessel wall to effectively cover the opening. In a preferred embodiment, the covering member 40 has a length of about 8.6 mm (in a 6 French system). Other dimensions are also contemplated.

It should be appreciated that alternatively the covering member could be provided with an enlarged width region as illustrated in the embodiment of FIG. 1 of the '141 application. The covering member could also be configured asymmetrically so that the enlarged region is off-centered to accommodate widening of the aperture as the member is pulled at an angle. The covering member could also be configured in a paddle shape with a narrowed region adjacent a wider region as in FIGS. 9B-9E of the '141 application. Other covering member configurations including those disclosed in the '141 application could be utilized with the retainers of the present application.

The elongated covering member can be composed of materials such as polycarbonate or polyurethane. Preferably it is composed of resorbable materials such as lactide/glycolide copolymers that after a period of time resorb in the body. If composed of resorbable material, the covering member could optionally have regions of varying resorbability. Varying degrees of resorbability can be achieved for example by utilizing different materials having differing resorbable characteristics or by varying the mass of the covering member (increased mass increases resorbtion time).

Retainers 20 and 22 are preferably composed of resorbable material. The retainers could alternatively be made of non-absorbable polymeric or metallic material.

When the retainers 20 and 22 are released from the delivery instrument, they are spaced further from the covering member 40. They are configured to then be advanced toward the covering member 40. More specifically, each retainer 20, 22 is fixedly secured to a respective flexible connecting member illustratively in the form of suture 30, 32. Sutures 30, 32 are preferably made of polymeric material and are preferably resorbable, preferably composed of a material such as polydioxanone. It is also contemplated that alternatively a metallic material could be utilized.

As shown, suture 30 has a free end 30a and an opposite end 30b secured to retainer 20 by molding, gluing, forming a knot, or other methods. Similarly, suture 32 has a free end 32a and an opposite end 32b secured to retainer 22 in a similar manner. The sutures 30, 32 are looped through the covering member 40. Other methods of attachment are also contemplated. For example, the sutures can be attached to covering member by a loop of suture as shown for example in FIG. 8 of co-pending patent application Ser. No. 12/854,988, filed Aug. 12, 2010, (hereinafter the "'988 application") incorporated herein by reference in its entirety.

To advance the retainers 20, 22 toward the vessel wall (and covering member 40), the free end 30a, 32a of each suture 30, 32 is pulled proximally (in a direction of the arrows of FIG. 4, thereby moving the respective retainer in the opposite direction closer to the aperture and vessel wall. Once tightened against the tissue, a sufficient retention force is maintained, i.e. a proximal pulling force on the covering member 40 to pull it slightly upwardly (proximally) against the vessel wall. The retainers 20, 22 therefore help to prevent the covering member 40 from separating from the vessel wall (e.g. moving in the direction toward the opposing vessel wall) which could create an unwanted gap between the covering member 40 and the vessel opening to allow blood flow. The extent to which the retainers 20, 22 move toward the wall (and thus their distance from the vessel wall in their final placement position) will depend on the tissue thickness. Thus, the closure device can adjust for different tissue thicknesses and apply a constant retention force regardless of tissue thickness.

The delivery instrument for inserting the closure device extends through an opening in the skin, through the tissue tract to the vessel, through an external opening in the vessel wall, through the aperture in the vessel wall, and through an internal opening on the internal side of the vessel wall into the vessel lumen.

The covering member 40 is outside a retainer tube and within a delivery sheath in a tilted position in a manner similar to FIGS. 2 and 3 of the '988 application. The covering member 40 emerges from the sheath and moves from a tilted and preferably a somewhat straightened positioned, (substantially aligned with the longitudinal axis of the sheath) to a transverse position within the vessel (see the orientation of FIG. 4). (Note the vessel wall is shown in FIG. 4 but the rest of the vessel and tissue are removed for clarity.) The retainers 20, 22 remain within the tube. Note the covering member 40 can be ejected by a pusher (not shown) contacting the side or top wall of the covering member As shown in FIG. 4, covering member 40 is pulled proximally to abut the internal opening on the internal side of the vessel W to cover (patch) the opening and the sutures 30, 32, extend through the opening A in the vessel wall. The first retainer 20 is ejected from the sheath by advancing the retainer 20, retracting the sheath or relative movement of both. The second retainer 22 is still within the tube. The second retainer 22 is then deployed in a similar manner as retainer 20, i.e. by relative movement of the sheath and retainers. Note that in the delivery position, the retainers 20 and 22 are preferably in a stacked relationship (not shown) to minimize the transverse dimension of the delivery system.

Then, to retain the covering member 40 in position against the vessel wall to block blood flow therethrough, sutures 30 and 32 are pulled proximally from their free ends 30a, 32a, in the direction of the arrows of FIG. 4 thereby advancing the retainers 20, 22 distally in the direction toward the aperture A and vessel wall W and covering member 40. As shown, the retainers 20, 22 can be moved to a position contiguous to the vessel wall, or depending on tissue thickness, may be adjacent the wall with some tissue interposed between the retainers and vessel wall. The retainers 20, 22 in this position apply a proximal (upward) force on the elongated covering member 40 to limit movement of the covering member 40 into the vessel. The retainers in this placement position are preferably in a substantially side by side relationship as shown in FIG. 4.

The covering member 40 has a first pair of holes 44a, 44b and a second pair of holes 46a, 46b. The first pair of holes 44a, 44b receive suture 32 and the second pair of holes 46a, 46b receive suture 30. Holes 44b, 46b have a smaller diameter than holes 44a, 46a, respectively. The larger hole 46a is dimensioned to receive suture 30 for free unrestricted movement of the suture 30 therethrough and therefore easier application of retainer 20. Similarly, the larger hole 44a is dimensioned to receive suture 32 for free unrestricted movement of the suture 32 therethrough and therefore for easier application (movement) of retainer 22. Smaller hole 46b is dimensioned to frictionally engage suture 30 so that tension is applied to the suture 30. It is dimensioned so that the suture 30 can be pulled through the hole 46b if sufficient force is applied by pulling on free end 30a, but if such predetermined force is not applied, the suture 30 will remain frictionally engaged within the wall of the hole 46b and not move. In this manner, when the user ceases pulling on free end 30a, the suture 30 and thus the retainer 22 will remain in position. Suture 32 operates in a similar manner, with smaller opening 44b dimensioned to frictionally engage and resist movement of the suture 32 to retain retainer 20 and allowing movement if a predetermined force is applied. FIG. 3 shows how the suture 30 is looped through the respective opening.

To enhance the retention of the suture of the present invention within the smaller diameter hole, a plurality of internal teeth can be provided. This is shown for example in FIGS. 22 and 23 of the '988 application wherein hole 496a' has a plurality of teeth 497 formed on the interior wall of the smaller opening. Engagement of the suture 430' by the teeth 497 retains the suture and spherical retainer. Note that the teeth can be formed to angle inwardly so the suture can be moved in only one direction, i.e. proximally, so the retainer is advanced toward the covering member.

As shown in FIG. 4, in the side by side relationship, the retainers 20 and 22 are alongside in a transverse orientation with respect to covering member 40. That is, they are positioned along the width of the covering member 40. However it is also contemplated that in the placement position, the retainers 20, 22 (and the retainers of the other embodiments disclosed herein) can be in a lengthwise orientation (substantially parallel to the longitudinal axis of the covering member). The retainers could also be in other side by side arrangements at angles to the longitudinal axis.

The alternate embodiment of FIG. 5 is identical to the embodiment of FIG. 1 except for the configuration of the retainers. Thus, closure device 100 has sutures (flexible connecting members) 130, 132 identical to sutures 30, 32 and a covering member or patch 140 identical to patch 40, with openings 146a, 146b and 144a, 144b identical to openings 46a, 46b, 44a, and 44b. Therefore, further detail of these components and their function for brevity will not be repeated herein. The retainers 120, 122 differ from retainers 20, 22 in that they are substantially cylindrical in shape. Retainers 120, 122 can optionally have a substantially planar upper surface, 121, 123, respectively, although other surfaces e.g. curved, irregular, can be provided.

The alternate embodiment of FIG. 6 is identical to the embodiment of FIG. 1 except for the configuration of the retainers. Thus, closure device 200 has a covering member or patch 240 identical to patch 40, sutures (flexible connecting members) 130, 132 identical to sutures 30, 32 and openings 246a, 246b and 244a, 244b in covering member 240 identical to openings 46a, 46b. 44a, and 44b. Therefore, further detail of these components and their function for brevity will not be repeated herein. The retainers 220, 222 differ from retainers 20, 22 in that they are substantially pill shaped.

In the embodiment of FIG. 7, hole closure device 300 has a patch 340 substantially identical to patch 40 except two openings instead of four are provided. Opening 342a is larger than opening 342b and is dimensioned to receive suture 330. That is, suture 330 extends through openings 342a and 344b. Opening 342b has a smaller dimension to frictionally engage the suture as described above with respect to FIG. 1 to restrict movement unless a predetermined force is applied. Retainers 320, 322 are substantially bullet shaped as in FIG. 1, but it is also contemplated other shaped retainers could be utilized, e.g. cylindrical, pill shaped, etc.

Retainers 320, 322 are joined by a flexible connecting or joining suture (member) 336 attached at opposite ends to the retainers by molding, welding or other methods. The joining suture 336 is received in looped portion 334 of suture (flexible connecting member) 330. Looped portion 334 is formed by a portion of the suture 330 extending from the patch 340, looping around twice and extending back into opening 342b (see FIG. 8). The end of the suture portion has a knot 346 (FIG. 8) which retains the suture 330. When suture free end 330a is pulled proximally, the loop 334 tightens around joining suture 336 and then pulls the joining suture 336 and thus the retainers 320, 322 toward the covering member 340. Note that since the retainers 320, 322 are connected together, a single suture moves the retainers 320, 322 toward the patch.

In the embodiment of FIG. 9, a single retainer 420 is provided in the form of a disc shaped member. Disc shaped member 420 is attached to a first portion of suture (flexible connecting member) 430 by a suture loop 432 looped through openings in the retainer 420. Suture 430 extends through small opening 444b in patch 440, exiting larger opening 444a. Thus, free end 430a of suture 430 is pulled proximally, pulling retainer 420 toward covering member 440, with the smaller opening 444b frictionally retaining the suture 430 in the same manner as in FIG. 1, unless a predetermined force is applied. Covering member 440 is identical to covering member 40.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A device for closing an aperture in a vessel wall, the aperture having an external opening in an external region of the vessel wall and an internal opening in an internal region of the vessel wall, the device comprising:
   a covering member having a longitudinal axis and positionable inside the vessel against the internal opening of the aperture, the covering member having a dimension to prevent egress of fluid through the aperture;
   first and second retainers positionable external of the vessel and being movable independently, the first and second retainers being one of substantially cylindrical and substantially pill shaped;
   a first flexible connecting member operatively connecting the first retainer to the covering member, the first flexible connecting member movable proximally to advance the first retainer toward the covering member and;
   a second flexible connecting member operatively connecting the second retainer to the covering member, the second flexible connecting member movable proximally to advance the second retainer toward the covering member.

2. The device of claim 1, wherein the covering member has a first opening configured to restrict movement of the first connecting member and a second opening spaced from the first opening configured for unrestricted movement of the first connecting member.

3. The device of claim 1, wherein the covering member and first and second retainers are composed of a resorbable material.

4. The device of claim 1, wherein the first and second retainers are positioned in a stacked relationship in a delivery position.

5. The device of claim 1, wherein the covering member is pivotable between a more longitudinal orientation for delivery and a transverse position for placement.

6. The device of claim 1, wherein the first and second retainers are fixedly secured to the respective first and second connecting members and independently movable toward the covering member while maintaining their position with respect to the respective connecting member.

7. The device of claim 6, wherein the first and second flexible connecting members are sutures, and the first and second retainers and the first and second flexible connecting members are composed of a resorbable material.

8. The device of claim 1, wherein the first and second retainers in a placement position to retain the covering member are positioned in a substantially side by side relationship such that inner side surfaces of the first and second retainers are closer than outer side surfaces, the side surfaces extending between lower and upper surfaces of the first and second retainers.

9. A device for closing an aperture in a vessel wall, the aperture having an external opening in an external region of the vessel wall and an internal opening in an internal region of the vessel wall, the device comprising:
   a covering member having a longitudinal axis and positionable inside the vessel against the internal opening of the aperture, the covering member having a dimension to prevent egress of fluid through the aperture;
   first and second retainers positionable external of the vessel and proximal of the covering member, the first and second retainers each having a body of a first transverse dimension and having a substantially cylindrical configuration with a longitudinal axis transverse to the longitudinal axis of the covering member in a placement position; and
   a first flexible connecting member operatively connecting the covering member and the first retainer and a second flexible connecting member operatively connecting the covering member and the second retainer, the first flexible connecting member movable to move the first retainer toward the covering member and the second flexible connecting member movable to move the second retainer toward the covering member, the first and second flexible connecting members being independently movable.

10. The device of claim 9, wherein the covering member has a first opening and a second opening spaced from the first opening, the first opening configured to restrict movement of the first connecting member and the second opening configured to restrict movement of the second connecting member.

11. The device of claim 9, wherein the covering member, the first and second flexible connecting members and the first and second retainers are composed of a resorbable material.

12. The device of claim 9, wherein the first and second retainers in a placement position to retain the covering member are positioned in a substantially side by side relationship such that inner side surfaces of the first and second retainers are closer than outer side surfaces, the side surfaces extending between lower and upper surfaces of the first and second retainers.

13. A device for closing an aperture in a vessel wall, the aperture having an external opening in an external region of the vessel wall and an internal opening in an internal region of the vessel wall, the device comprising:
   a covering member having a longitudinal axis and positionable inside the vessel against the internal opening of the aperture, the covering member having a dimension to prevent egress of fluid through the aperture, the covering member having a first opening and a second opening;
   first and second retainers positionable external of the vessel and proximal of the covering member in a placement position, the first and second retainers each having a body having a substantially cylindrical configuration, the first and second retainers being independently movable toward the covering member; and
   a first flexible connecting member operatively connecting the covering member and the first retainer, the first flexible connecting member being fixedly secured to the first retainer at one end wherein the first flexible connecting member is movable to move the first retainer toward the covering member as a second end of the first flexible connecting member is moved proximally, the first retainer remaining fixedly secured to the first flexible connecting member at the first end to maintain its position on the first flexible connecting member as it is moved toward the covering member, the second opening in the covering member configured to enable unrestricted movement of the first flexible connecting member through the second opening and the first opening in the covering member configured to restrict movement of the first flexible connecting member until a predetermined force is applied.

14. The device of claim 13, further comprising a second flexible connecting member operatively connecting the covering member and the second retainer, the second flexible connecting member being fixedly secured to the second retainer at one end wherein the second flexible connecting member is movable to move the second retainer toward the covering member as a second end of the second flexible connecting member is moved proximally, the second retainer remaining fixedly secured to the second flexible connecting member at the first end to maintain its position on the second flexible connecting member as it moved toward the covering member, and the first and second flexible connecting members being independently movable.

15. The device of claim 13, wherein the first and second openings are of different sizes to receive the first flexible connecting member and the covering member includes third and fourth openings of different sizes to receive the second flexible connecting member.

16. The device of claim 15, wherein the first and third openings frictionally engage the first and second flexible connecting members and the second and fourth openings are dimensioned for free unrestricted movement of the first and second flexible connecting members.

17. The device of claim 16, wherein the second opening has a larger cross-sectional dimension than the first opening and the fourth opening has a larger cross-sectional dimension than the third opening.

18. The device of claim 13, wherein the covering member, first and second flexible connecting members and first and second retainers are composed of resorbable material.

* * * * *